United States Patent [19]

Popescu et al.

[11] Patent Number: 5,154,930
[45] Date of Patent: Oct. 13, 1992

[54] PHARMACOLOGICAL AGENT-LIPID SOLUTION PREPARATION

[75] Inventors: Mircea C. Popescu, Plainsboro; Paul A. Tremblay, Hamilton, both of N.J.; Andrew S. Janoff, Yardley, Pa.; Marc J. Ostro, Princeton, N.J.; Elaine Chan, Willow Grove, Pa.; Alan Weiner, Lawrenceville, N.J.

[73] Assignee: The Liposome Company, Inc., Princeton, N.J.

[21] Appl. No.: 160,141

[22] Filed: Feb. 25, 1988

Related U.S. Application Data

[63] Continuation-in-part of Ser. No. 22,156, Mar. 5, 1987, abandoned.

[51] Int. Cl.$^5$ .............. A61K 9/14; A61K 9/48; A61K 9/66; A61K 31/685
[52] U.S. Cl. ..................... 424/489; 424/1.1; 424/450; 424/452; 424/455; 424/456; 424/492; 428/402.2; 436/829; 514/78; 514/885; 514/937
[58] Field of Search ............ 428/402.2; 424/450, 424/452, 455, 456, 492, 489; 514/962, 78, 885, 937; 436/829

[56] References Cited

U.S. PATENT DOCUMENTS

| | | | |
|---|---|---|---|
| 4,053,585 | 10/1977 | Allison et al. | 424/92 |
| 4,117,113 | 9/1978 | Allison et al. | 424/89 |
| 4,235,871 | 11/1980 | Papahadjopoulos et al. | 264/4.6 X |
| 4,438,052 | 3/1984 | Weder et al. | 264/4.6 |
| 4,460,577 | 7/1984 | Moro et al. | 424/79 X |
| 4,483,873 | 11/1984 | Ohashi et al. | 514/788 X |
| 4,619,794 | 10/1986 | Hauser | 264/4.1 |
| 4,649,047 | 3/1987 | Kaswan | 424/78 |
| 4,714,571 | 12/1987 | Tremblay et al. | 260/403 |
| 4,861,580 | 8/1989 | Janoff et al. | 424/1.1 |

FOREIGN PATENT DOCUMENTS

| | | | |
|---|---|---|---|
| 85402254.8 | 11/1985 | European Pat. Off. | |
| 56315 | 5/1978 | Japan | 514/78 |
| 2135268 | 8/1984 | United Kingdom | 424/450 |
| WO87/07506 | 12/1987 | World Int. Prop. O. | |

OTHER PUBLICATIONS

Lachman et al., :*The Theory and Practice of Industrial Pharmacy,* Third Edition, Lea & Febiger, Philadelphia, (1986), p. 402.

The Lipid Handbook, Edited by Frank D. Gunstone et al., Chapman and Hall, Ltd., London, 1986, p. 29.

Deamer, et al., "Large Volume Liposomes by an Ether Vaporization Method" Biochim. Biophys. Acta., 443:629-634.

*Primary Examiner*—Richard D. Lovering
*Attorney, Agent, or Firm*—Allen Bloom; Ilene Janofsky

[57] ABSTRACT

A pharmacological agent-lipid solution preparation comprising a lipophilic pharmacological agent, a desalted charged lipid and an aqueous-miscible lipid solvent such that upon introduction into an aqueous medium a suspension of lipid aggregates associated with the pharmacological agent are formed, and methods of manufacture and use.

39 Claims, 2 Drawing Sheets

PHARMACOLOGICAL AGENT-LIPID SOLUTION PREPARATION

This application is a continuation-in-part of U.S. patent application Ser. No. 22,156, filed Mar. 5, 1987 now abandoned.

FIELD OF THE INVENTION

This invention discloses a pharmacological agent-lipid solution preparation comprising a lipophilic pharmacological agent, a desalted charged lipid, and an aqueous-miscible lipid solvent such that upon introduction into an aqueous medium a suspension of lipid associated with the pharmacological agent is formed. Further disclosed are preparation and methods of manufacture and use of the pharmacological agent-lipid solution preparation, and the co-solubilizing of lipid associating pharmocological agent in lipid and ethanol solution.

BACKGROUND OF THE INVENTION

Lipids are known to be useful as carriers for the delivery of drugs to mammals including humans. In pharmaceutical preparations lipids are variously used as admixtures with drugs or in the form of liposomes.

Liposomes are vesicles comprising closed bilayer membranes containing an entrapped aqueous phase. Liposomes may be any variety of unilamellar vesicles (possessing a single membrane bilayer) or multilamellar vesicles (e.g. onion-like structures characterized by concentric membrane bilayers, each separated from the next by an aqueous layer).

Liposomes are formed by methods well known in the art. The original liposome preparation of Bangham et al. (1965, *J. Mol. Biol.* 13:238-252) involves suspending phospholipids in an organic solvent which is then evaporated to dryness leaving a phospholipid film on the reaction vessel. Then an appropriate amount of aqueous phase is added, the mixture is allowed to "swell", and the resulting liposomes which consist of multilamellar vesicles are dispersed by mechanical means. The structure of the resulting membrane bilayer is such that the hydrophobic (nonpolar) "tails" of the lipid orient toward the center of the bilayer while the hydrophilic (polar) "heads" orient toward the aqueous phase. This technique provides the basis for the development of the small sonicated unilamellar vesicles described by Papahadjopoulos and Miller (1967, *Biochim. Biophys. Acta.* 135:624-638) and large unilamellar vesicles.

Another class of liposomes is characterized as having substantially equal interlamellar solute distribution. This class of liposomes is denominated as stable plurilamellar vesicles (SPLV) as defined in U.S. Pat. No. 4,522,803 to Lenk et al. and includes monophasic vesicles as described in U.S. Pat. No. 4,588,578 to Fountain et al. and frozen and thawed multilamellar vesicles (FATMLV) as described in "Solute Distributions and Trapping Efficiencies Observed in Freeze-Thawed Multilamellar Vesicles," Mayer et al., *Biochima et Biophysica Acta.* 817:193-196 (1985).

Another method of liposome formation is by the infusion of lipid solvent such as diethyl ether or ethanol which contains phospholipids into an aqueous solution containing a pharmacological agent resulting in the formation of liposomes which entrap a portion of the aqueous solution. This procedure cannot be used to entrap lipid soluble pharmacological agents soluble in fat or fat solvents due to the very limited solubility of such agents in an aqueous solution.

Lipid soluble pharmacological agents include antineoplastics such as doxorubicin; antifungals such as miconazole, terconazole and amphotericin B; immunomodulators such as cyclosporin A; derivatives of muramyl dipeptides such as muramyl tripeptide phosphatidylethanolamine; and, hormones such as glucocorticoids, mineralocorticoids and estrogens; anti-inflammatories such as the steroidals, prednisone, dexamethasone and fluromethasone and the nonsteroidals indomethacin, salicylic acid acetate (aspirin) and ibuprofen, further including analgesic agents such as acemetacin and flurobiprofen; and other agents such as lipoxygenase inhibitors, prostaglandins, neuroleptics, antidepressants, fat-soluble vitamins, contrast materials and antivirals. Pharmacological agents as used herein includes agents administered to animals including mammals, particularly humans, in the course of treatment or diagnosis. Biologically active materials such as drugs as well as diagnostic agents and contrast materials which are usually nonreactive are all to be understood to be pharmacological agents.

Solubilization of lipid soluble pharmacological agent-lipid suspension preparation in water is usually done with the help of solubilizing agents such as polyethylene glycols and propylene glycol, or via surfactants including such well known surfactants as polysorbates, poloxamers, and polyethoxylated castor oil. Upon administration, however, these agents may be present in concentrations sufficient to induce undesirable side effects.

To avoid the use of such agents, D. Schmidt (U.S. Pat. No. 4,271,196) proposed colloidal suspensions formed by solubilization of lipids in ethanol, removal of the solvent by evaporation and addition of water or buffer with the drug added before water or in the colloidal suspension of lipids. Similarly, J. Schrank and H. Steffen (U.S. Pat. No. 4,411,894) solubilized both lipids and drug in ethanol, then ethanol was removed and buffer was added to form liposomes.

These and other procedures involving the removal of ethanol and liposome formation have two major disadvantages. First, ethanol cannot solubilize certain lipids; in particular, salt forms of acidic, or basic phosphatides ("charged phosphatides") such as phosphatidic acid, dicetylphosphate, phosphatidylethanolamine, and phosphatidylserine. Second, the entrapment of lipophilic drug in liposomes is limited such that the drug/lipid ratio (wt/wt) is usually less than 0.2.

It is to be understood that neutral lipids are those which do not present a charge at neutral pH. Phospatidylcholine having a zwitterionic group is termed a neutral polar lipid and compounds such as cholesterol or triglycerides are nonionizable at physiological pH's and are termed neutral nonpolar lipids.

To increase the efficacy of drug solubilization by the lipids, F. Tsunekazu et al. (European Pat. No. 0161445A1) proposed the solubilization of lipids and drug in an organic solvent, removal of the organic solvent, homogenization of the resulting film in aqueous solution by ultrasonic treatment, centrifugation of the suspension and recovery of the lower most layer of the sediment, to yield a particular drug-phospholipid complex. In this publication, particular reference is made to drugs having a molecular weight below 1,000.

Lipid preparations such as liposomes carrying pharmacological agent-lipid solution agents are often characterized by having insufficient shelf life. Dried liposome preparations have been offered to overcome this problem however such preparations must be reconstituted at the time of use. Reconstitution may be associated with problems of clumping and uncertainty as to the liposomal size of the reconstituted preparation, and uncertainty as to the strength of an aliquot. These preparations are also associated with rapid sedimentation.

It is an object of this invention to provide a pharmacological agent-lipid solution preparation in high drug to lipid ratio.

It is a further object of this invention to provide a pharmacological agent-lipid solution preparation wherein the pharmacological agent is of a molecular weight of greater than about 1000.

It is another object of this invention to provide a pharmacological agent-lipid solution preparation sterilizable by filtration.

It is an additional object of this invention to provide a pharmacological agent-lipid solution preparation of lipophilic pharmacological agent.

It is another object of this invention to provide a pharmacological agent-lipid solution preparation that will form a suspension of lipid associated with said pharmacological agent upon introduction into an aqueous medium and further that such suspension exhibit a stability of at least 0.25 to 6 hours or longer without sedimentation and preferably at least about 2 hours.

It is a further object of this invention to provide a method of forming such suspension.

It is another object of this invention to provide a method of treating mammals, including humans, with therapeutically effective amounts of such suspension.

SUMMARY OF THE INVENTION

This invention comprises a pharmacological agent-lipid solution preparation comprising a lipophilic pharmacological agent, a desalted charged lipid and an aqueous miscible lipid solvent. This preparation, upon introduction into an aqueous medium, forms a suspension of lipid associated with the pharmacological agent. In some embodiments the pharmacological agent-lipid solution preparation may be in an oral dosage form such as a unit oral dosage form including tablets, capsules, dragees, and troches which is to include methods of treating subjects employing such dosage forms. The suspended lipid associated with pharmacological agent will be termed an aggregate.

This invention further comprises such preparation wherein the desalted charged lipids are desalted charged phosphatides such as phosphatidic acid, dicetylphosphate, phosphatidylethanolamine, and phosphatidylserine.

Further encompassed are pharmacological agent-lipid solution preparations which are both pharmaceutically acceptable and of limited flammability preferably by use of less volatile lipid solvents or by admixture of a first lipid solvent with secondary less flammable solvents such as polyethylene glycol (about 400-800 mw being preferred) and propylene glycol. Particularly preferred are preparations of at least about 10% (wt/wt) polyethylene glycol (about 800 mw) with about 30% most preferred.

Additionally encompassed by this invention is the nonaqueous water-miscible lipid solvent being absolute ethanol.

Further entailed in this invention is the lipid soluble pharmacological agent being an immunomodulator such as cyclosporin A; an anti-neoplastic such as doxorubicin; an antifungal such as miconazole, terconazole, and amphotericin B; an anti-inflammatory such as the steroidal anti-inflammatories prednisone, doxamethasone, fluoromethasone and the nonsteroidal anti-inflammatories such as indomethacin, salicylic acid acetate, ibuprofen; and the derivatives of muramyl dipeptide such as muramyl tripeptide phosphatidylethanolamine, and hormones such as glucocorticoids, mineralocorticoids and estrogens.

Particularly included in this invention are anti-inflammatories in unit oral dosage form including tablet, capsule, dragee, or troche, and methods of treating subjects employing such dosage forms.

Included in this invention is a preparation wherein the pharmacological agent is indomethacin is present from about 0.5% to about 30% by weight, and more particularly present at from about 10 to about 20% by weight, perticularly in unit dosage forms, and also wherein the lipid is additionally comprised of at least about 70% by weight phosphatidylcholine.

In another embodiment polypeptides having a molecular weight of greater than about 1000, such as cyclosporin A or insulin, are the pharmacological agents.

A further embodiment of the invention is the method of preparing a suspension from the pharmaceutical agent-lipid liquid solution preparation by adding the preparation to pharmaceutically acceptable aqueous medium. This is preferably added at a ratio of at least about 0.1:1 v/v. This method utilizes the pharmaceutical agent-lipid liquid preparations with all of the above noted lipids, solvents, and pharmaceutical agents.

The aqueous media used in the method of preparation include water, 5% dextrose in water (wt/v), 0.9% saline, physiological phosphate buffer, and physiological citrate buffer.

Yet further this invention encompasses suspensions of the pharmacological agent-lipid solution preparation in aqueous media wherein the pharmacological agent to lipid ratio is at least about 20 moles percent.

This invention further includes a method of treating animals (including humans) in need of such treatment comprising the step of administering to the animal a therapeutically effective amount of pharmacological agent-lipid solution preparation added to a pharmaceutically acceptable aqueous medium thus forming a suspension. This administration is preferably parenteral, intramuscularly, intraperitioneally, intravenously, subcutaneously, or topically, via inhalation, or oral administration including suppository, or ingestion. The pharmacological agents of this method of administration will be any of those noted above and others. The lipids of this method of administration will be any of those noted above and others.

An included method of treatment comprises treating animals (including humans) in need of such treatment comprising the step of administering to the animal a therapeutically effective amount of the pharmacological agent-lipid solution preparation such as by oral administration of such preparation, particularly in unit dosage form such as tablets, capsules, troches or dragees.

Further included is a method of increasing the solubility of a lipid soluble pharmacological agent in lipid solvent (particularly ethanol) and lipid by the process of co-solubilizing said agent in a co-solution of lipid and lipid solvent. The invention includes the lipid comprising at least about 10% by weight of the ethanol:lipid co-solution. In one embodiment the lipid comprises phosphatidylcholine. The method also includes the agent being a nonsteroidal anti-inflammatory, such as indomethacin or salicylic acid acetate.

Also included is pharmacological preparation comprising absolute ethanol, lipid, and nonsteroidal anti-inflammatory, particularly wherein the nonsteroidal anti-inflammatory is indomethacin, and wherein the indomethacin is present from about 0.5% to about 30% by weight and wherein the indomethacin is present at from about 10 to about 20% by weight.

DETAILED DESCRIPTION OF THE INVENTION

Figure 1:
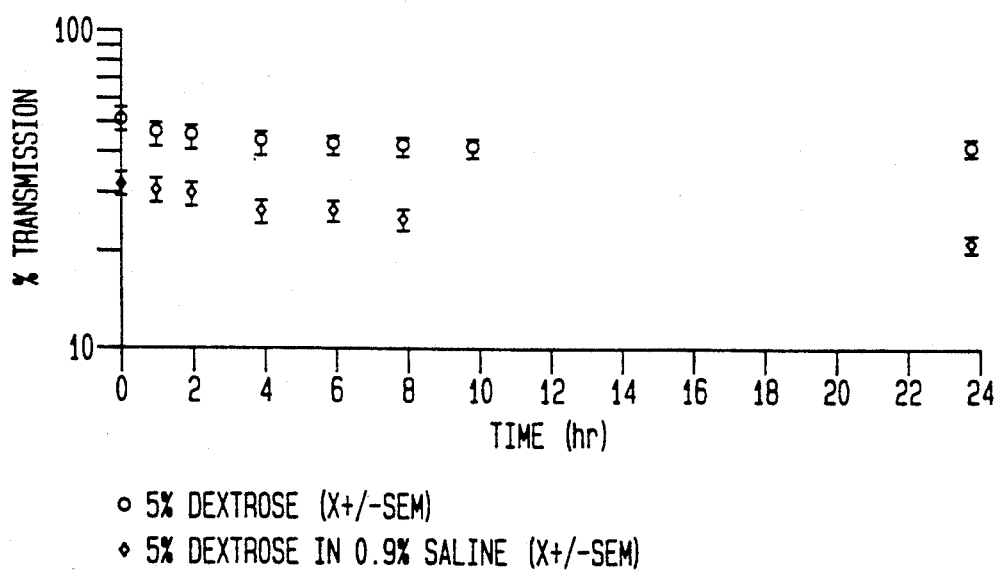
FIG. 1 plots turbidimetric measurements of suspensions of cyclosporin dextrose or in dextrose in saline as against time.

The "pharmacological agent-lipid solution preparations" of this invention first comprise at least one lipophilic pharmacological agent, as well as a lipid solvent, and at least one lipid. Lipophilic (or lipid soluble) as defined herein includes along with true lipid solubility, the capacity to closely associate with lipids.

Lipid soluble pharmacological agents include respiratory agents such as theophyllin, anti-epileptics such as diphenylhydantoin, anti-neoplastics such as doxorubicin; antifungals such as miconazole, terconazole and amphotericin B, (some antifungals will require desalting and or a acidification of the lipid solvent to increase solubility); immunomodulators such as cyclosporin A; derivatives of muramyl dipeptides such as muramyl tripeptide phosphatidylethanolamine; and, hormones such as glucocorticoids, mineralocorticoids and estrogens; anti-inflammatories such as the steroidals, prednisone, dexamethasone and fluromethasone and the non-steroidals such as indomethacin, salicylic acid acetate and ibuprofen, further including analgesic agents such as acemetacin and flurobiprofen, and other agents such as lipoxygenase inhibitors, prostaglandins, neuroleptics, antidepressants, fat-soluble vitamins, contrast materials and antivirals.

Other preferred nonsteroidal anti-inflammatories are:
carboxylic acids
salicylates
    Acetylsalicylic Acid (i.e., Salicyclic Acid Acetate)
    Salsalate
    Diflunisal
    Fendosal
Acetic Acids
    Indomethacin
    Acemetacin
    Cinmetacin
    Sulindac
Tolmetin
    Zomepirac
    Diclofenac
    Fenclofenac
    Isoxepac
    Furofenac
    Fentiazac
    Clidanac
    Oxepinac
    Fenclorac
    Lonazolac
    Metiazinic Acid
    Clopirac
    Amfenac
    Benzofenac
    Clometacine
    Etodolac
    Bumidazone
    Clamidoxic Acid
Propionic Acids
    Ibuprofen
    Flurobiprofen
    Naproxen
    Ketoprofen
    Fenoprofen
    Benoxaprofen
    Indoprofen
    Pirprofen
    Carprofen
    Oxaprozin
    Pranoprofen
    Suprofen
    Microprofen
    Tioxaprofen
    Alminoprofen
    Cicloprofen
    Tiaprofenic Acid
    Furaprofen
    Butibufen
    Fenbufen
    Furobufen
    Bucloxic Acid
    Protizinic Acid
Fenamates
    Mefanamic Acid
    Flufenamic Acid
    Meclofenamate
    Niflumic Acid
    Tolfenamic Acid
    Flunixin
    Clonixin
Pyrazoles
    Phenylbutazone and Analogs
    Peprazone (Prenazone)
    Apazone (Azapropazone)
    Trimethazone
    Mofebutazone
    Kebuzone
    Suxibuzone
Oxicams
    Piroxicam
    Isoxicam
    Tenoxicam Indomethacin is a most preferred nonsteroidal anti-inflammatory. In the preparations of this invention, indomethacin preferably comprises from about 0.5% to about 30% of the final weight of the pharmacological agent-lipid solution preparation, and particularly from about 10 to about 20%, and most particularly about 15%.

It is a limitation of this invention that at least one lipid be charged and desalted, and such desalted charged lipids are (a) soluble in the water miscible lipid solvents of this invention and (b) exhibit only a limited tendency for sedimentation upon dispersal in the aqueous medium of suspension formation.

Lipid materials used in this invention are amphipathic in character. Amphipathic as defined herein is a moiety with a hydrophobic portion and a hydrophilic portion.

Hydrophilic character will be imparted to a molecule through the presence of phosphatidic, carboxylic, sulphatic, amino, sulfhydryl, nitro, and other groups such as carbohydrates. Hydrophobicity will be conferred by the inclusion of groups that include, but are not limited to, long straight and branched chain saturated and unsaturated aliphatic hydrocarbon groups and such groups substituted by one or more aromatic, cycloaliphatic or heterocyclic group. The preferred amphipathic compounds are phosphoglycerides, representative examples of which include phosphatidylcholines, phosphatidylethanolamines, lysophosphatidylcholines, lysophosphatidylethanoloamines, phosphatidylserines, phosphytidylinositols, phosphatidic acids, phosphatidylglycerols and diphosphatidylglycerols as well as sphingomyelins. Synthetic saturated compounds such as dimyristoylphosphatidylcholine and dimyristoylphosphatidylglycerol or unsaturated species such as dioleoylphosphatidylcholine or dilinoleoylphospatidylcholine are also usable. Other compounds lacking phosphorous, such as members of the glycolipids, and glycosphingolipid, ganglioside and cerebroside families, are also within the group designated as amphipathic lipids. Salts of acid derivatives of sterols and tocopherols such as cholesterol or tocopherol hemisuccinate are also amphipathic. Ionic detergents such as octadecanylsulfonate are also included.

Salts of acidic or basic lipids (i.e., charged lipids) that otherwise are not soluble in ethanol can be rendered soluble by desalting, that is by removal of the counterion. For example phosphatidic acid, phosphatidylserine, dicetylphosphate, phosphatidylglycerol and phosphatidylethanolamine may be desalted. Natural soy or egg phosphatides may be desalted and the resulting desalted mixture of various lipids will contain sufficient desalted charged lipids in the form of acidic phospholipids for use in this invention. Thus in the practice of this invention, the presence of an amount of neutral lipids, polar or nonpolar, along with desalted charged lipids will not adversely affect the preparation. The tolerable amount of neutral lipid is limited by the solubility of the various lipids in water-miscible lipid solvent system and the required stability of the suspension formed upon mixture with the aqueous medium. Thus, a critical element of this invention is the presence of a desalted charged lipid. The minimum amount of desalted charged lipid will vary with the system. However, at minimum at least sufficient desalted charged lipid must be present to form a stable suspension. Each system will present a different minimum amount of charged lipid necessary for stability but, by way of example, desalted phosphatidic acid will be effective in a presence as low as about 0.5 mole percent relative to total lipid in a cyclosporin A-ethanol system. The desirable amount of desalted charged lipid for other systems is easily determined with reference to the solubility of proposed lipid in the solvent system and the required stability of the final aqueous suspension.

Desalting of lipids is accomplished by exchanging the counterion from the acidic or basic moiety of the amphipathic lipid for a proton or hydroxide, respectively. This is done by any of a number of methods well known in the art including ion exchange resin column elution.

The typical ion exchange resin procedure employs commercially available resins such as those of the Biorad Company of Richmond, Va. A typical cation exchange resin is Biorad AG50-X8 and Biorad AG1-X8 is a typical anion exchange resin. These procedures, performed in the aqueous-soluble lipid solvent itself, are relatively insensitive to temperature and pressure and are conveniently performed at ambient or room temperature (i.e., about 22.5° C. +/− about 2.5° C.) and atmospheric pressure.

Lipids used in this invention are obtainable from a number of sources. Natural phosphatide mixtures from egg or soy containing more than 70% phosphatidylcholine are obtained from a number of commercial sources such as Sigma Chemical of St. Louis, MO, and Lipoid KG, Ludwigshafen, West Ger., Hepar of Franklin, Ohio. Hepar supplies egg phosphatidylcholine. Other sources of lipid such as soy phosphatidylcholine are American Lecithin, Woodside, L.I., NY, and Riceland Foods, Little Rock, Ark. Phosphatidic acid of 99% purity is obtained from Avanti Chemical of Birmingham, AL.

A method for desalting utilizes trichlorofluromethane ($CCl_3F$) (E.I. du Pont de Nemours & Co., Wilmington, Del., under the trademark Freon 11). In this method phosphatides are added to a mixture of absolute ethanol and $CCl_3F$ at a ratio of from about 0.5:1 to 1:0.5 with 1:1 being most preferred to form a solution. A temperature of 15° C. is preferred at atmospheric pressure but any temperature below the boiling point of $CCl_3F$ at the operating pressure is suitable, particularly 20°-35° C. under pressure.

About 5 g of phosphatide may be added to about 40 ml of the $CCl_3F$/ethanol mixture but this proportion may be increased and is limited only by the formation of emulsion upon making of two phases. Up to about a 20 wt % mixture of phosphatide:$CCl_3F$/ethanol solvent may be used with about 1-10 wt % being preferred. The resulting solution is titrated with a slight excess of dilute acid such as HCl and the solution is mixed by any convenient method including stirring, shaking and sonication. The slight emulsion formed is permitted to separate and usually this requires only a matter of minutes.

The $CCl_3F$ layer is removed and an ethanol:water (about 2:1-1:2 ethanol:water v/v) mixture is then added to the $CCl_3F$ solution for repeated washing and removal of excess acid, until the upper phase is neutral. The lower $CCl_3F$ solution is then warmed to about room temperature (i.e., about 22.5° C. +/− about 2.5° C.) to evaporate the $CCl_3F$ leaving the desalted lipid residue. Care is required in warming so that frothing does not occur. The solvent is then removed. This is conveniently accomplished first by evaporation with a thin stream of nitrogen at about 22.5° C. +/− about 2.5° C. and then by rotoevaporation. Again care is taken so that frothing/bumping does not occur.

The lipid solvents of this invention must be (1) dissolving of lipids, (2) substantially soluble (termed herein "miscible") in water, and (3) pharmaceutically acceptable. As the lipid solvent will only appear in the administered dose upon dilution by the aqueous phase and the dilution would ordinarily constitute about a 5 to 50 times reduction in lipid solvent concentration a number of pharmaceutically acceptable lipid solvents are available. These include ethanol, polyethylene glycol and propylene glycol. The preferred polyethylene glycols have molecular weights of about 400 to 800 with about 800 most preferred. Absolute ethanol is the preferred lipid solvent, but any pharmaceutically acceptable lipid solvent may be used.

The lipid solvent must be miscible or at least significantly soluble with the aqueous solution in order to deliver simultaneously both the pharmacological agent and lipid to this solution as well as for the purpose of diluting the lipid solvent in the aqueous solution.

The lipid solvents for the solution preparation must be substantially water free but water miscible. The presence of excess water in the preparation will cause the lipophilic pharmacological agents to be insoluble and can adversely affect the storage stability of the preparation through hydrolysis. The maximum amount of water will vary with the specific agent but generally will be less than about 1% and not greater than about 5% or 10% (w/w). In practice the maximum amount of water tolerable in a system is easily determined in that if excess water is present the solution becomes cloudy indicating the presence of precipitate or liposomes. Certain pharmacological agents susceptable to hydrolysis such as salicylic acid acetate do not tolerate the presence of water even at about 5% in ethanol, though lesser amounts of water are tolerable in this system. Substantially water-free lipid solvents wherein the pharmacological agent-lipid is not appreciably hydrolized or rendered insoluble will be termed nonaqueous.

Due to the high flammability of absolute ethanol, admixing with at least about 10% lipid solvent diluent such as polyethylene glycol 400 or 800 is preferred and up to about 30% polyethylene glycol 800 most preferred in reducing flammability of the preparation while maintaining pharmaceutical acceptability. Other weights of polyethylene glycol and other lipid solvent diluents are also acceptable.

Sterility of drug-lipid solution is necessary both for a prolonged shelf life as well as subsequent use of this solution. Therefore, drug-lipid solution is conveniently terminally sterilized by filtration. This is preferably done through a 0.2 micron polycarbonate filter, cellulose-containing filter or other inert filter that does not interact either with lipid solvent or with the solubilized drug or lipid. Filtration also removes undissolved particles from the preparation. Sterilization by filtration is a particular advantage of this preparation.

Storage stability of the pharmocological agent-lipid solution preparation will vary but is directly related to the stability of the lipids. The storage stability is enhanced by storing at reduced temperatures.

The pharmacological agent-lipid solution may be advantageously employed by direct administration wherein a suspension will be formed in vivo wherein the aqueous medium is the physiological environment. In such application a pharmacological agent-lipid solution, such as indomethacin mixed with a non-aqueous water-miscible lipid solvent such as ethanol and a desalted charged lipid, when ingested, conveniently in capsule or liquid form, becomes liposomal in the gastric environment. Other suitable oral dosage forms are dragees, troches, lozenges, tablets and additional forms known to those skilled in the art. Oral dosage forms configured and adapted for oral administration to subjects in need of such dosages shall be termed unit oral dosage forms.

Aggregate suspensions prepared from the pharmacological agent-lipid solution preparation are made by agitating the preparation in an aqueous medium. Agitation is accomplished by any convenient method, but is most easily accomplished by loading the solution preparation into a syringe and then injecting the preparation into the aqueous medium as contained within an ampoule or container. The exact rate of injection is not critical. Injection of the solution preparation should be accompanied by rapid mixing such that the water miscible lipid solvent and the aqueous medium rapidly mix. Beyond the syringe method other convenient methods of preparing the suspension are pouring, dropping, or spraying in while hand mixing, vortexing, stirring or sonicating.

Any pharmaceutically acceptable aqueous medium may be used. Examples of suitable aqueous media are water, 5% dextrose in water, physiological citrate buffer, physiological phosphate buffer and 0.9% saline. As used here in referring to physiological buffers indicates pharmaceutical acceptability in view of the intended use in animals such as mammmals (including humans). The use of such medium will be both for formation of the suspension and as a pharmaceutical diluent. For oral administration the preferred aqueous medium is water or palatable fluids such as fruit juices and syrups or infusions such as teas and coffee.

At moderate pharmacological agent to lipid ratios pharmacological agent-lipid solution will generally form aggregates in the structure of liposomes upon mixing with aqueous medium.

At higher pharmacological agent to lipid ratios, the aggregate structure becomes nonliposomal. For example, at pharmacological agent to lipid ratios of about 1:1 (wt/wt), the aggregates are spherical particles of about 0.2 $\mu$m or higher, have minimal entrapped water, appear to be temporarily closely associated with the water miscible lipid solvent, and upon centrifugation appear denser than liposomes of similar pharmacological agent and lipid composition. Higher pharmacological agent to lipid ratios will be understood to mean from about 20 moles percent pharmacological agent to lipid ratio up to about 60 moles percent or more.

The formation of aggregates upon formation of suspension is strongly related to the pharmacological agent/lipid ratio (wt/wt) of the solution preparations. Examination of this ratio was done from about 10:1 to about 0.5:1. In general, aggregate diameter and suspension opacity decreased as less lipid in relation to pharmacological agent was utilized.

At the higher pharmacological agent to lipid ratios, the aggregates were of submicron size and the suspensions colloidal, thus the physical parameters of the suspenson are adjustable by varying the ratios of the pharmacological agent to lipid.

Preparations of pharmacological agent-lipid solution such as those with cyclosporin A used in this invention are preferably begun by the dissolving of the agent and/or the lipid into lipid solvent. While this can conveniently be accomplished at about 22.5° C.+/− about 2.5° C., using a heated water bath, facilitates dissolving. For cyclosporin A, a water bath at about 40° C.–50° C. facilitates the dissolution.

Generally, lipids and pharmacological agent are separately solubilized into lipid solvent as stock solutions at convenient concentrations. Stock solutions can be maintained at convenient and nondegrading temperature, for example 4° C. When preparing a particular pharmacological agent-lipid solution preparation of the present invention appropriate aliquots of stock solutions were combined to achieve desired final concentrations of lipid and agent.

However, it is quite acceptable to add pharmacological agent and lipid directly to the lipid solvent of a preparation. In such circumstance it is preferable to add the lipid to the lipid solvent first as the lipid in some circumstances increases the solubility of a pharmacological agent. This co-solubilizing or "salting-in" may be up to about a 50% increase in solubility or apparent solubility with agents such as salicylic acid acetate and indomethacin. In the context of salting in the term "apparent solubility" recognizes that a pharmacological agent salted in may be in the form of a complex with dissolved lipid rather than truly solubilized, such as is the case with amphotericin B.

The co-solubilizing or salting in is a surprising aspect of this invention as to pharmacological agents that will associate with lipid. Lipid soluble pharmacological agents include the nonsteroidal anti-inflammatories such as salicylic acid acetate and indomethacin as noted above. To practice this aspect of the invention requires dissolving lipid in the lipid solvent, such as ethanol, forming a co-solution prior to addition of the pharmacological agent to be co-solubilized. From about 10% lipid by weight up to the solubility limit of the particular lipid (or lipids) in the lipid solvent may be used as the solution in which to co-solubilize the lipid soluble (or apparently soluble) pharmacological agent.

After the solution of lipid and lipid solvent is made diluents such as polyethylene glycol (which may also be a lipid solvent) can be added to reduce flammability. Antioxidants may also be added then. The final pharmacological agent-lipid solution preparation is conveniently stored in an ampoule and preferably at about 4° C.

The pharmacological agent-lipid solution preparation concentration of constituents will only be limited by the relative solubility of such constituents with a view to the desired final concentration. A typical preparation will be comprised of up to about 0.5 gm of drug/ml of lipid solvent with about 0.5 gm of lipid.

In the preferred pharmacological agent-lipid solution preparation storage stability is enhanced by the inclusion of an antioxidant such as alpha-tocopherol. This is present in amounts at about 0.1 to about 1% (wt/wt) relative to the amount of lipid.

To determine whether phospholipids can increase the solubility or apparent solubility of a pharmacological agent such as salicylic acid acetate, both drug and lipid were co-solubilized in a lipid solvent such as absolute ethanol (USP). Five ml of this lipid solvent was able to dissolve about a maximum of 1 gr. salicylic acid acetate. A lipid such as egg phosphatidylcholine was completely dissolved in 5 ml of ethanol in a series of test tubes and to this solution crystals of the test pharmacological agent salicylic acid acetate were added gradually and dissolved. The maximum amount of salicylic acid acetate dissolved in 5 ml ethanol containing 1.5 gm egg phosphatidylcholine was about 1.5 gm indicating about a 50% increase in solubility of drug under these conditions. Any convenient temperature and pressur may be used for this procedure that will dot adversely affect the pharmacological agent or boil the lipid solvent.

This "salting in" illustrates for one skilled in the art the use of lipids for increasing the solubility of lipid soluble drugs up to 50% or more. Salicylic acid acetate solubility in an egg phosphatidylcholine ethanol is seen to increase about 50% and the solubility of indomethacin in a similar system is seen to increase about 50%. Amphoteracin B is similarly salted in but appears to do so in the form of complexes with lipid rather than simple solubilizing.

A number of analytical steps known in the art are useful in selecting those lipid/lipid solvent systems which upon mixture with an aqueous medium, generate pharmaceutically acceptable suspensions. Such analytical steps include assessment by visual inspection for appearance, opacity and the presence of crystals, precipitates or sediment; (b) light microscopic examination such as in a Neubauer cytometer with a micrometer scale at 100 times and 400 times magnification; (c) turbidimetric measurements by assessing transmission at 520 nm; (d) electron microscopy of negatively stained preparations; (e) quasielastic light scattering (QELS) for determination of mean particle dimension; (f) ultracentrifugation; (g) organ distribution after intravenous innoculation of aggregate suspension having aggregates labeled with a reporting group such as a radioactive tracer, (e.g., $^3$H-cyclosporin when using cyclosporin); and (h) bioactivity in cell culture of a particular cell type (e.g., for cyclosporin, spleen lymphocytes stimulated with concanavaline A and labeled with $^3$H-thymidine).

In addition, such suspensions must be without large aggregations, precipitates or crystals. The suspension must remain free of large aggregations precipitates or crystals during the time necessary for preparing and administering injections under hospital conditions. This time was presumed to be at minimum from about 15 minutes to about two hours. For the suspensions intended for intravenous administration, selection for small aggregate size is necessary as suspensions containing bodies, such as aggregates, over 5 microns in diameter are not usually suitable for intravenous administration. Thus, those skilled in the art may rapidly define a lipid solvent system suspension suitable for internal and particularly intravenous administration.

The results of organ distribution of aggregates showed that the aggregates do not accumulate in liver and spleen as would be predicted for liposomes.

The pharmacological agent-lipid solution preparations of this invention are useful for treating animals (including humans) in need of such treatment. Treatment as used herein includes administration of any pharmacological agents such as diagnostic materials, biologically active agents and contrast materials.

Treatment is frequently accomplished by preparing a suspension from the solution preparation and administering the suspension in therapeutically effective amounts. However, as noted, the pharmacological agent-lipid solution may be directly administered for treating mammals. A therapeutically effective amount will be understood to mean a sufficient amount to achieve a physical or physiological response, and for known drugs will generally be the same dose for the existing dosage forms of the drug.

The therapeutically effective amount of a given pharmacological agent will vary with the purpose of the administration, the particularities of the recipient and other factors well known in the art.

In a liposome-drug delivery system, a pharmacological agent such as a drug is entrapped in or associated with the liposome and then administered to the patient to be treated. For example, see Rahman et al., U.S. Pat. No. 3,993,754; Sears, U.S. Pat. No. 4,145,410; Paphadjopoulos et al., U.S. Pat. No. 4,235,871; Schneider, U.S. Pat. No. 4,114,179; Lenk et al., U.S. Pat. No. 4,522,803; and Fountain et al., U.S. Pat. No. 4,588,578.

The mode of administration of the preparation may determine the sites and cells in the organism to which the compound will be delivered. Aggregates of this invention can be administered alone but will generally be administered in admixture with a pharmaceutical carrier selected with regard to the intended route of administration and standard pharmaceutical practice. The preparations may be injected parenterally, for example, intra-arterically or intravenously. The preparations may also be administered via oral, subcutaneous, or intramuscular routes, or by inhalation. For parenteral administration, they can be used, for example, in the form of a sterile aqueous solution which may contain other solutes, for example, enough salts or glucose to make the solution isotonic. Other uses, depending upon the particular properties of the preparation, may be envisioned by those skilled in the art.

For administration to humans in the curative treatment of disease states, the prescribing physician will ultimately determine the appropriate dosage for a given human subject, and this can be expected to vary according to the age, weight, and response of the individual as well as the nature and severity of the patient's disease. The dosage of the drug in aggregate form will generally be about that employed for the free drug. In some cases, however, it may be necessary to administer doses outside these limits.

This invention will be better understood by reference to the following examples which are merely illustrative of the invention.

EXAMPLE 1

Cyclosporin A Solution Preparation:Desalted Lipids

Stock solution of cyclosporin A (Sandoz Pharmaceuticals Corporation, East Hanover, NJ) at 200 mg/ml and stock solution of desalted egg phosphatides (Hepar Industrial, Inc., Franklin, Ohio) at 250 mg/ml were prepared in advance and kept at 4° C. To prepare 10 ml of cyclosporin-lipid solution 2 ml of lipid stock solution was brought up to 8.75 ml with absolute ethanol and mixed by hand at about 22.5° C.+/− about 2.5° C. and atmospheric pressure. To this solution 1.25 ml of cyclosporin A stock was added and mixed again. The final solution containing cyclosporin 25 mg/ml and desalted egg phosphatides 50 mg/ml was filtered through 0.2 micron polycarbonate filter. The solution was then bubbled through with oxygen free nitrogen for 10 seconds, overlayed with nitrogen and tightly enclosed.

EXAMPLE 2

Cyclosporin A Solution Preparation:Desalted and Neutral Lipids 1.25 gm of dry powdered egg yolk phosphatides (nondesalted) (Hepar) were dissolved in 2 ml absolute ethanol by heating at 56° C. for 10 min. in a water bath. The solution was then cooled in a ice basket and filtered through a 1.0 micron polycarbonate filter (Nucleopore, Pleasanton, CA). The resulting lipid solution was adjusted to a concentration of 400 mg lipids/ml with absolute ethanol. Desalted phosphatidic acid was dissolved in ethanol at a concentration of 200 mg/ml. 0.63 ml of the egg yolk phosphatide solution was mixed with 0.63 ml of a cyclosporin A-ethanol solution containing 200 mg cyclosporin/ml drug to which was then added 0.06 ml of desalted phosphatidic acid ethanol solution followed by mixing. All mixing steps took only a matter of minutes. The resulting mixture was adjusted to 5 ml with absolute ethanol to a final concentration of 50 mg egg phosphatides, 6.25 mg desalted phosphatidic acid and 25 mg cyclosporin A per ml ethanol. This solution was sterilized by filtration through 0.2 micron polycarbonate filter (Nucleopore, Pleasanton, CA), bubbled through with oxygen-free nitrogen and sealed in an ampoule.

EXAMPLE 3

Cyclosporin A Solution Preparation and Suspension

Soy phosphatidylcholine after removal of absolute ethanol insoluble impurities and being desalted was dissolved in absolute ethanol at about 22.5° C.+/− about 2.5° C. and atmosphereic pressure at a concentration of 382 mg/ml. Cyclosporin A was dissolved in a separate aliquot of absolute ethanol at a concentration of 200 mg/ml.

The cyclosporin A-lipid solution was prepared by adding sequentially in a glass tube 0.327 ml lipid solution (125 mg), 1.25 ml cyclosporin A Solution (250 mg), absolute ethanol 1.87 ml (1.47 gm) and 6.50 ml (7.34 gm) polyethylene glycol 400.

After each addition solutions were briefly shaken and the final solution was vortexed. This solution contained 50 mg cyclosporin A, and 25 mg lipid in 1 ml of 65% polyethylene glycol 400 in absolute ethanol.

A suspension was formed by adding 20 mg of this solution by injection into 500 ml 5% dextrose in water. The aggregates in the suspension thus formed were 1.0 micron or smaller.

The aggregates including the aggregates in suspension were assessed by: (a) visual inspection for appearance, opacity and presence of concretions, crystals, precipitates or sediment; (b) light microscopic examination in a Neubauer cytometer with a micrometer scale at 100 times and 400 times magnification; (c) turbidimetric measurements by assessing transmission at 520 nm; (d) electron microscopy of negatively stained preparations; (e) quasielastic light scattering (QELS) for determination of mean particle dimension; (f) ultracentrifugation; (g) organ distribution after intravenous innoculation of aggregate suspension having aggregates labeled with $^3$H-cyclosporin; and (h) bioactivity in cell culture of spleen lymphocytes stimulated with concanavaline A and labeled with $^3$H-thymidine.

QELS analysis indicated that the mean diameter of aggregates was below 0.3 microns (Table 1). Turbidimetric measurements of suspensions kept at about 22.5° C.+/− about 2.5° C. without agitation showed that the transmission at 520 nm gave similar value at "zero" time (shortly after suspension was formed) and at subsequent time points (FIG. 1) indicating a rapidly forming and stable suspension.

Figure 2:
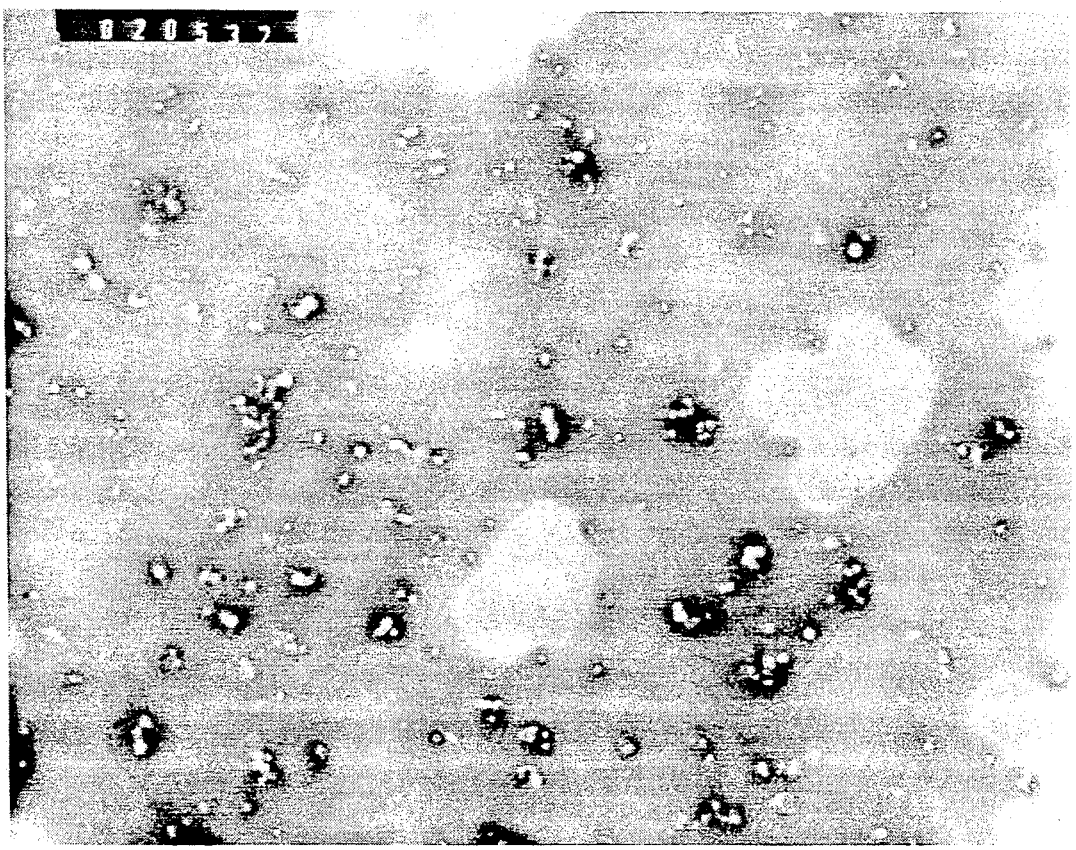
FIG. 2 is an electron microscopy of round droplet-like particles having a diameter below 1.0 micron of the aggregates of the instant invention.

Electron microscopy revealed round droplet-like particles having a diameter below 1.0 micron in agreement with light microscopy examination and QELS results (FIG. 2). All three measurements clearly showed that the dimension of aggregates can be modulated by changing the pharmaceutical agent/lipid ratio and the nature of the lipids used.

Ultracentrifugation analysis showed that the aggregates sediment when the suspension is placed over a Hypaque-Ficoll solution diluted one-third with distilled water and having a density higher than 1.0. Under the same preparation and centrifugation conditions, liposomes formed by dispersion of lipids alone in aqueous medium, do not sediment.

EXAMPLE 4

Cyclosporin A Suspension

A sample for parenteral administration from the solution of Example 1 was prepared by taking the content of an ampuole (10 ml ethanol containing 500 mg egg phosphatides which were desalted and 250 mg cyclosporin A with a #23G needle (1.5 in) adapted to a 10 ml syringe. The needle was inserted through the rubber stopper of a 500 ml bottle containing 5% dextrose in water. The bottle was kept upside down and mixed by hand to create a vortex, while the contents of the syringe was infused over 20 seconds continuously into the aqueous solution. After injection was completed, the needle was retracted and the bottle shaken by hand for 10 sec. The resulting aggregates, the cyclosporin A-lipid suspension, was allowed to stand for 15 minutes to allow disappearance of the gas bubbles formed during shaking. This suspension was intended for use within 15 min. to 6 hrs after preparation.

EXAMPLE 5

Cyclosporin Behavior in vivo

Cyclosporin A aggregates were slightly more efficacious in suppressing lymphocyte proliferation as measured by $^3$H-thymidine uptake, than the cyclosporin solubilized in polyethoxylated castor oil and ethanol.

The dimensions of the nonliposomal lipid aggregates wherein the pharmacological agent is cyclosporin A are relatively uniform of a size about 250 nm +/− 20 nm.

The results of organ distribution of aggregates showed that the aggregates do not accumulate in liver and spleen as would be predicted for liposomes.

EXAMPLE 6

Aspirin Solution Preparation

Desalted egg phosphatides (Hepar) were dissolved in ethanol at a concentration of 250 mg/ml in a 1000 ml flask. To 400 mg of salicylic acid acetate, 1.6 ml of the above solution containing 400 mg of phosphatides was added and the solution adjusted with absolute ethanol to 4 ml. The final concentration of both ingredients in this pharmacological agent-lipid solution was 100 mg/ml. This procedure was performed at about 22.5° C.+/− about 2.5° C. and atmospheric pressure.

EXAMPLE 7

Aspirin Suspension

To prepare a suspension, desalted egg phosphatides (Hepar) were dissolved in ethanol at a concentration of 250 mg/ml in a 1000 ml flask. To 400 mg of salicylic acid acetate, 1.6 ml of the above solution containing 400 mg of phosphatides was added and the solution adjusted with absolute ethanol to 4 ml. The final concentration of both ingredients in this pharmacological agent-lipid solution was 100 mg/ml. This procedure was performed at about 22.5° C.+/− about 2.5° C. and atmospheric pressure. Then 0.5 ml of the salicylic acid acetate-lipid solution was added to 9.5 ml of distilled water and briefly shaken by hand, at about 22.5° C.+/− about 2.5° C. and atmospheric pressure forming a suspension. The resulting suspension was milky in appearance and did not contain visable crystals or aggregates after a 30 minute period. Light microscopy of the suspension revealed aggregates, primarily with a diameter below 5 microns and no crystal characteristic for salicylic acid acetate. This suspension contained 0.5 mg salicylic acid acetate/ml.

EXAMPLE 8

Topical/Oral Aspirin Suspension

A dosage form of salicylic acid acetate for topical or oral use was prepared as follows: Desalted egg phosphatides (Hepar) were dissolved in absolute ethanol at a concentration of 250 mg/ml in a 1000 ml flask. To 400 mg of salicylic acid acetate, 1.6 ml of the above solution containing 400 mg of phosphatides was added and the solution adjusted with absolute ethanol to 4 ml. The final concentration of both ingredients in this pharmacological agent-lipid solution was 100 mg/ml. This procedure was performed at about 22.5° C.+/− about 2.5° C. and atmospheric pressure. Next, the topical/oral administration dosage form was prepared by adding the pharmacological agent-lipid solution, to water at about 22.5° C.+/− about 2.5° C. and briefly agitating the mixture. A cloudy suspension promptly formed. This salicylic acid acetate formulation may then be ingested or used topically.

EXAMPLE 9

Indomethacin Preparation 15 g of egg phosphatides (Lipoid E80, Lipoid KG, Ludwigshafen, West Ger.) containing 80% phosphatidylcholine was solubilized in 3 ml absolute ethanol. The resulting co-mixture then solubilized indomethacin, 1 g of which was then added to the co-mixture. The final preparation contained 25 mg of indomethacin and 375 mg of lipid per 0.4 ml. This precedure was performed at about 22.5° C.+/− about 2.5° C. at and atmospheric pressure. The ethanol concentration of the preparation was 0.075 ml/0.4 ml. The preparation was encapsulated in a soft gelatin capsule as a unit oral dosage form.

PREPARATION 1

Desalting of Lipids: Hexane-Ethanol-Hydrochloric Acid Procedure

Natural phosphatide mixtures from soy containing more than 70% phosphatidylcholine (PC) were dissolved in hexane at 1 gm lipid/10 ml solvent. To this solution 6.6 ml of absolute ethanol and 3.3 ml of 0.2N HCl was added and mixed thoroughly at atmospheric pressure and at about 22.5° C.+/− about 2.5° C. Phase formed and were permitted to separate and the lower aqueous phase discarded. The hexane phase was repeatedly washed with ethanol-water, 1:1 (v/v) until the pH in the lower aqueous phase was neutral. The resulting desalted lipids were recovered from the hexane phase by removal of the hexane by rotoevaporation at 35° C. and 100 mm Hg.

PREPARATION 2

Desalting of Lipids:CCl$_3$F

At atmospheric pressure and in a cold room (4°-10° C.) 5 grams of egg phosphatides (Hepar) were dissolved in a mixture of absolute ethanol:CCl$_3$F (Freon 11, du Pont), 1:1 (40 ml) at 15° C.; 25 ml of 0.5N aqueous HCl was added and the mixture shaken The lower CCl$_3$F phase was removed after the emulsion was broken and mixed with 20 ml of absolute ethanol and 25 ml of water. The CCl$_3$F lower phase was again removed and the ethanol/water wash was repeated until the upper aqueous phase was neutral. The lower CCl$_3$F solution was allowed to warm to about 22.5° C.+/− about 2.5° C.

and the solvent driven off with a stream of nitrogen and finally, on a rotoevaporator. Yield=4.9 grams of desalted lipids.

PREPARATION 3

Desalted Lipids:Ionic Exchange Resin 20 gm of egg phosphatides (Hepar) dissolved in 100 ml of absolute ethanol was passed through 200 g of the cation exchange resin (Biorad of Richmond, Va) (AG 50 WX8) in the hydrogen form and in ethanol. The column was further diluted with 50 ml of ethanol, at about 22.5° C.+/− about 2.5° C. and atmospheric pressure. The total eluant of the first volume was passed through 200 g column of anion exchange resin (Biorad AG1-X8) in the hydroxyl form and in ethanol. The columns were washed with 50 ml of absolute ethanol and the total 200 ml of eluant contained desalted phospholipids at a concentration of 10 g/100 ml of ethanol. This was useable directly or diluted further with ethanol.

PREPARATION 4

Salting In

Five ml of absolute ethanol was able to dissolve maximum 1 gr. salicylic acid acetate. Egg phosphatidylcholine (Hepar) 1.5 gm was completely dissolved in 5 ml of ethanol in a series of test tubes and to this solution crystals of salicylic acid acetate were added gradually and dissolved. The maximum amount of salicylic acid acetate dissolved in 5 ml ethanol containing 1.5 gm egg phosphatidylcholine was 1.5 gm indicating a 50% increase in solubility of drug. To accelerate the dissolving process all test tubes containing crystals of salicylic acid acetate and lipid solvent were agitated gently in a water bath of 40° C. and cooled to about 22.5° C.+/− about 2.5° C. after crystals were completely dissolved.

TABLE 1

| QELS ANALYSIS OF AGGREGATE DIMENSION | | |
|---|---|---|
| | MEAN DIAMETER (nm) | |
| SAMPLE | NICOMP ANALYSIS* | GAUSSIAN ANALYSIS |
| HDrrC4-33 | 129.0 | 150.0 |
| HDrrC5-34 | 183.00 | 144.0 |
| HDrrC6-35 | 258.00 | 176.7 |
| HDrrC7-36 | 209.00 | 143.4 |
| JDrrC1-37 | 166.0 | 151.4 |
| X ± S: | 189.0 ± 48 | 153.0 ± 13 |

*NICOMP analysis is a data reduction extracting the component sizes contributing to the exponential curve.

We claim:

1. A pharmacological agent-lipid solution preparation comprising
   (a) a desalted charged lipid
   (b) a nonaqueous water-miscible lipid solvent
   (c) a lipid soluble pharmacological agent.
2. The preparation of claim 1 wherein the desalted charged lipid is phosphatidic acid, dicetylphosphate, phosphatidylethanolamine or phosphatidylserine.
3. The preparation of claim 1 wherein the solvent comprises at least about 10% (wt/wt) polyethylene glycol of molecular weight of from to about 400 to 800.
4. The preparation of claim 3 wherein the solvent further comprises about 30% polyethylene glycol of molecular weight of from about 400 to about 800 (wt/wt).
5. The preparation of claim 1 wherein the solvent comprises absolute ethanol.
6. The preparation of claim 1 wherein the pharmacological agent is an immunomodulator, an antifungal, anti-inflammatory, antineoplastic agent or hormone.
7. The preparation of claim 6 wherein said agent is a polypeptide having a molecular weight of greater than about 1000.
8. The preparation of claim 6 wherein the pharmacological agent is an immunomodulator.
9. The preparation of claim 8 wherein the immunomodulator is cyclosporin A.
10. The preparation of claim 6 wherein the pharmacological agent is an antifungal agent.
11. The preparation of claim 10 wherein the antifungal agent is miconazole, terconazole or amphotericin B.
12. The preparation of claim 6 wherein the pharmacological agent is an antineoplastic.
13. The preparation of claim 12 wherein the antineoplastic is doxorubicin.
14. The preparation of claim 6 wherein the pharmacological agent is a hormone.
15. The preparation of claim 14 wherein the pharmacological agent is a glucocorticoid, mineralocorticoid or estrogen.
16. The preparation of claim 6 wherein the pharmacological agent is an anti-inflammatory.
17. The preparation of claim 16 in a unit oral dosage form.
18. The preparation of claim 16 wherein the anti-inflammatory is prednisone, dexamethasone or fluoromethasone.
19. The preparation of claim 16 wherein the anti-inflammatory is indomethacin, salicylic salicylic acid acetate ibuprofen.
20. The preparation of claim 19 wherein the anti-inflammatory is indomethacin.
21. The preparation of claim 20 additionally comprising at least about 70% by weight phosphatidylcholine.
22. The preparation of claim 20 wherein the indomethacin is present from about 0.5% to about 30% by weight.
23. The preparation of claim 22 in unit dosage form.
24. The preparation of claim 22 wherein the indomethacin is present at from about 10 to about 20% by weight.
25. The preparation of claim 24 additionally comprising at least about 70% by weight phosphatidylcholine in unit dosage form.
26. The preparation of claim 1 in a unit oral dosage form.
27. The preparation of claim 1 further comprising (d) a pharmaceutically acceptable aqueous medium.
28. A method of treating an animal in need of such treatment comprising the step of administering a therapeutically effective amount of the preparation of claim 1.
29. A method of treating an animal in need of such treatment with the liquid preparation of claim 1 comprising the steps of:
   (a) adding said pharmacological agent-lipid solution preparation to a pharmaceutically acceptable aqueous medium forming a suspension; and
   (b) administering the resulting suspension to said animal in a theraputically effective amount.
30. The method of claim 29 wherein administration is parenteral intramuscularly, intraperitoneally, intravenously, subcutaneously, by inhalation, topically or orally.

31. The method of claim 29 wherein said lipid is phosphatidic acid, dicetylphosphate, phosphatidylethanolamine or phosphatidylserine.

32. The method of claim 29 wherein said pharmacological agent is an immunomodulator, an antifungal, anti-inflammatory, antineoplastic agent or hormone.

33. The method of claim 32 wherein said agent is an immunomodulator.

34. The method of claim 33 wherein said immunomodulator is cyclosporin A.

35. A method of treating an animal in need of treatment with an anti-inflammatory agent comprising the step of administering a therapeutically effective amount of the preparation of claim 16.

36. A method of preparing a suspension from the preparation of claim 1 comprising adding said preparation to a pharmaceutically acceptable aqueous medium.

37. The method of claim 36 wherein the preparation is added to the aqueous medium at a ratio of at least about 0.1:1 v/v.

38. The method of claim 36 wherein the aqueous medium is water, 5% dextrose in water, 0.9% saline, physiological phosphate buffer, or physiological citrate buffer.

39. The method of claim 36 wherein said suspension contains aggregates in which the concentration of pharmacological agent to lipid is at least about 20 mole percent.

* * * * *